(12) United States Patent
Kitade et al.

(10) Patent No.: US 10,006,024 B2
(45) Date of Patent: Jun. 26, 2018

(54) RNA INTERFERENCE AGENT, METHOD FOR PRODUCING SAME, AND USE THEREFOR

(71) Applicant: GIFU UNIVERSITY, Gifu-shi, Gifu (JP)

(72) Inventors: Yukio Kitade, Gifu (JP); Remi Nakashima, Gifu (JP)

(73) Assignee: GIFU UNIVERSITY, Gifu-shi (JP)

( * ) Notice: Subject to any disclaimer, the term of this patent is extended or adjusted under 35 U.S.C. 154(b) by 167 days.

(21) Appl. No.: 14/648,521

(22) PCT Filed: Nov. 29, 2013

(86) PCT No.: PCT/JP2013/082179
§ 371 (c)(1),
(2) Date: May 29, 2015

(87) PCT Pub. No.: WO2014/084354
PCT Pub. Date: Jun. 5, 2014

(65) Prior Publication Data
US 2015/0307878 A1    Oct. 29, 2015

(30) Foreign Application Priority Data
Nov. 29, 2012  (JP) ................... 2012-261730

(51) Int. Cl.
*C12N 15/113* (2010.01)
*C12Q 1/68* (2018.01)
*A61K 31/7125* (2006.01)
*A61P 43/00* (2006.01)
*C12N 15/11* (2006.01)

(52) U.S. Cl.
CPC .......... *C12N 15/113* (2013.01); *C12N 15/111* (2013.01); *C12Q 1/6897* (2013.01); *C12N 2310/11* (2013.01); *C12N 2310/14* (2013.01); *C12N 2310/3513* (2013.01); *C12N 2320/53* (2013.01); *C12N 2330/30* (2013.01)

(58) Field of Classification Search
USPC .......... 435/6.1, 6.11, 6.12, 91.1, 91.31, 455, 435/6.13; 514/44; 536/23.1, 24.5; 506/9
See application file for complete search history.

(56) References Cited

FOREIGN PATENT DOCUMENTS

| JP | 2001-519642 | A | 10/2001 |
|---|---|---|---|
| JP | 2008-532480 | A | 8/2008 |
| JP | 2009-504179 | A | 2/2009 |
| JP | 2009-530319 | A | 8/2009 |
| JP | 2010-538677 | A | 12/2010 |
| JP | 2011-511636 | A | 4/2011 |
| JP | 2011-171282 | A | 9/2011 |
| JP | 2012-509688 | A | 4/2012 |
| WO |  | 97/07224 A1 | 2/1997 |
| WO | 2006/071410 | A2 | 7/2006 |
| WO | 2007/021142 | A1 | 2/2007 |
| WO | 2007/094135 | A1 | 8/2007 |
| WO | 2007/107162 | A2 | 9/2007 |
| WO | 2009/039173 | A2 | 3/2009 |
| WO | WO 2009/039173 | * | 3/2009 |
| WO | 2009/102427 | A2 | 8/2009 |
| WO | 2010/062817 | A1 | 6/2010 |
| WO | 2011/084193 | A1 | 7/2011 |
| WO | 2011/085056 | A1 | 7/2011 |
| WO | WO 2011/084193 | * | 7/2011 |
| WO | 2011/119887 | A1 | 9/2011 |

OTHER PUBLICATIONS

Maiti et al, Chem. Eur. J., vol. 17, pp. 1519-1528 (2011).*
Ma et al, Nature, vol. 429, pp. 318-322 (2004).*
Somoza et al, Chem. Commun., vol. 46, pp. 4270-4272 (2010).*
J.B. Ma et al. "Structural Basis for Overhang-Specific Small Interfering RNA Recognition by the PAZ Domain." Nature vol. 429, pp. 318-322, 2004.
Maiti et al. "Structural and Binding Study of Modified siRNAs with the Argonaute 2 PAZ Domain by NMR Spectroscopy." Chemistry European Journal vol. 17, pp. 1519-1528, 2011.
Somoza et al. "Modified siRNAs for the Study of the PAZ Domain." Chemistry Communication vol. 46, pp. 4270-4272, 2010.
Mar. 4, 2014 International Search Report issued in International Patent Application No. PCT/JP2013/082179.
Nov. 29, 2013 International Preliminary Report on Patentability issued in International Patent Application No. PCT/JP2013/082179.
Jul. 11, 2016 Extended Search Report issued in European Patent Application No. 13858466.9.
Jun. 23, 2017 Office Action issued in European Patent Application No. 13 858 466.9.
Aug. 22, 2017 Office Action issued in Japanese Patent Application No. 2014-549919.
Bramsen, Jesper B., et al. "A Large-Scale Chemical Modification Screen Identifies Design Rules to Generate siRNAs with High Activity, High Stability and Low Toxicity." Nucleic Acids Research, vol. 37, No. 9, 2009, pp. 2867-2881.
Feb. 6, 2018 Office Action issued in European Patent Application No. 13858466.9.

\* cited by examiner

*Primary Examiner* — Jane Zara
(74) *Attorney, Agent, or Firm* — Oliff PLC

(57) ABSTRACT

Provided is an RNA interference agent, with which a suppression effect on the off-target effect can be obtained with a simple system. The disclosures relate to an RNA interference agent provided with a single-stranded oligonucleotide passenger strand having one or two or more PAZ domain low-affinity units at the 3'-end.

13 Claims, 10 Drawing Sheets

RNA interference agent (siRNA)
(a)
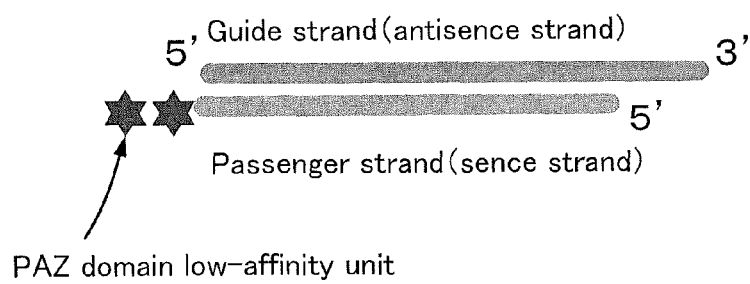
(b)
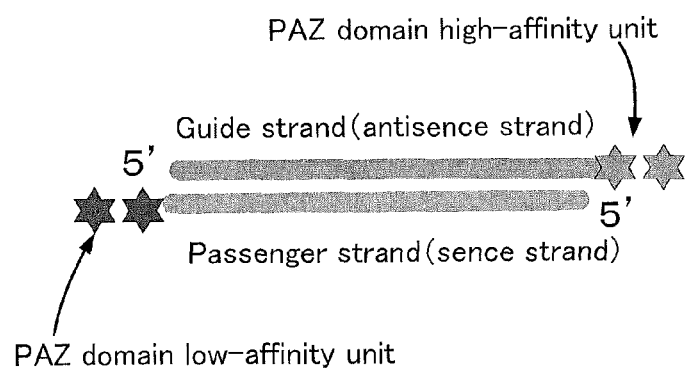
Fig.2

| Position of 3' end | Comparative examples | | | | | | | Examples | |
|---|---|---|---|---|---|---|---|---|---|
| | 1 | 2 | 3 | 4 | 5 | 6 | 7 | 1 | 2 |
| AB | TT | PB | n=2 | n=2 | n=4 | n=2 | n=2 | PB | TT |
| CD | TT | PB | n=3 | n=5 | n=5 | PB | TT | n=3 | n=2 |

| Position of 3' end | Comparative examples | | | | | | Examples |
|---|---|---|---|---|---|---|---|
| | 1 | 2 | 3 | 4 | 5 | 6 | 1 |
| AB | TT | PB | n=2 | n=2 | n=4 | n=2 | PB |
| CD | TT | PB | n=3 | n=5 | n=5 | PB | n=3 |

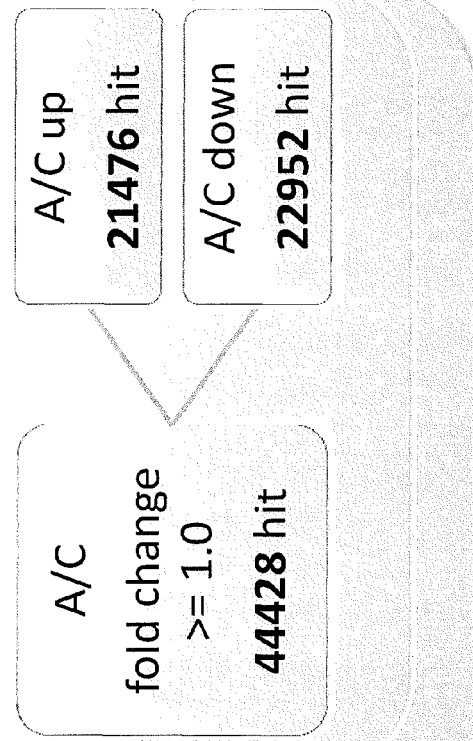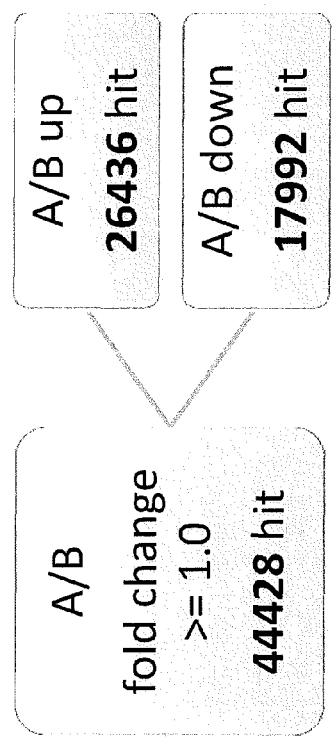
Fig.9

RNA INTERFERENCE AGENT, METHOD FOR PRODUCING SAME, AND USE THEREFOR

TECHNICAL FIELD

This description relates to an RNA interference (hereunder sometimes called simply "RNAi") agent, to a method for producing the same and to a use therefor and the like.

BACKGROUND ART

RNAi can cause sequence-specific decomposition of mRNA, suppressing expression of a target gene. siRNA and miRNA that cause RNAi hold promise for functional gene analysis and clinical applications because of their technical simplicity and strong gene suppression effects.

In the RNAi pathway, normally double-stranded siRNA or miRNA is incorporated into a protein complex called RISC in the cell, and dessociated into single strands. The strand that remains in the RISC and participates in gene expression is called the guide strand (antisense strand), while the other strand, which is released from the RISC, is called the passenger strand (sense strand). In the case of siRNA, when the guide strand is properly incorporated into the RISC, the RISC complex including the guide strand recognizes a target mRNA having a sequence complementary to the guide strand, and cleaves the target mRNA by agog slicer activity. In the case of miRNA, it recognizes the target mRNA and suppresses the translation process. It is thought that expression of the target gene is suppressed as a result.

It has been hypothesized that of the two strands, RISC distinguishes, as a guide strand, one of the strands from the other one of the strands by a mechanism involving the thermodynamic stability of both ends of the double strand.

In some cases, the passenger strand is incorporated as if the passenger strand were a guide strand. This produces a so-called "off-target" effect. The off-target effect is a phenomenon in which a gene other than the target gene is unintentionally suppressed. In RNAi, when the passenger strand is incorporated into the RISC, the nucleotide sequence of the passenger strand (which is complementary to the guide sequence) may act on the mRNA of a gene other than the original target gene, suppressing its expression.

One method that has been proposed for suppressing this off-target effect is to introduce a modified nucleotide into the passenger strand (Patent Literature 1). It has also been proposed that the passenger strand be provided with a discontinuous site (Patent Literature 2). Another proposal has been to promote incorporation of the antisense strand (guide strand) into the RISC by modifying the 2' hydroxy groups of the nucleotides of one or both ends of the sense strand (passenger strand) with methyl groups or the like (Patent Literature 3).

It is also known that the PAZ (Piwi/Argonaute/Zwille) domain of the RISC universally has a hydrophobic pocket, and a guide strand-RISC complex is formed by the interaction of the 3'-end of the guide strand with this hydrophobic pocket (Non Patent Literature 1).

CITATION LIST

Patent Literature

Patent Literature 1: Japanese Translation of PCT Application No. 2010-538677

Patent Literature 2: Japanese Translation of PCT Application No. 2009-530319

Patent Literature 3: Japanese Translation of PCT Application No. 2011-511636

Non Patent Literature

Non Patent Literature 1: J. B. Ma, K. Ye, D. J. Patel, Structural basis for overhang-specific small interfering RNA recognition by the PAZ domain, Nature 429, 318-320 (2004)

SUMMARY

However, introduction of a modified nucleotide into the passenger strand is normally a complicated process. Moreover, it has not been possible to completely ensure both the target gene suppression effect of RNAi and a suppression effect on the off-target effect.

Therefore, the disclosures of this description provide an RNA interference agent whereby an off-target effect suppression effect can be obtained with a simple system.

Solution to Technical Problem

The inventors deduced that an effective way to control the off-target effect (suppression of the expression of a gene other than the original target gene) in RNA interference would be to suppress incorporation of the 3'-end of the passenger strand (sense strand) into the PAZ domain. Therefore, the inventors introduced polar groups into the 3' ends of the guide strands and/or passenger strands of double-stranded RNA, and evaluated suppression of the off-target effect. As a result, it was shown that no RNAi effect was obtained with a single-stranded RNA having a polar group introduced into the 3'-end. Based on these findings, the disclosures of this description provide the following.

The disclosures of this description provide a single-stranded oligonucleotide provided with one or two or more PAZ domain low-affinity units at the 3'-end. This PAZ domain low-affinity unit may be represented by the following formula:

[Chem. 1]

$$[-X-Y-O-]_n \qquad \text{Formula(1)}$$

(where X is a linking group, Y represents a group with 2 or more carbon atoms, and n is an integer of or more). Y may also represent a group with 2 carbon atoms.

The PAZ domain low-affinity unit may also be a unit represented by the following formula for example.

[Chem. 2]

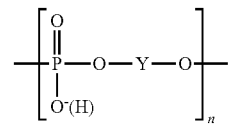

Preferably, two PAZ domain low-affinity units are provided at the 3'-end.

The disclosures of this description provide an RNA interference agent comprising: a guide strand oligonucleotide having an antisense site for a specific nucleotide sequence of a target gene; and a single-stranded oligonucleotide disclosed in this description, which is a passenger strand oligonucleotide that hybridizes specifically with the antisense site. A PAZ domain high-affinity unit may also be provided at the 3'-end of the guide strand oligonucleotide.

The PAZ domain high-affinity unit may also be represented by the following formula.

[Chem. 3]

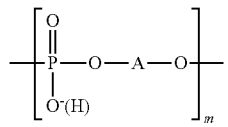

Formula(2)

(where A independently represents any of the following formulae, and m is an integer of 1, 2 or more).

[Chem. 4]

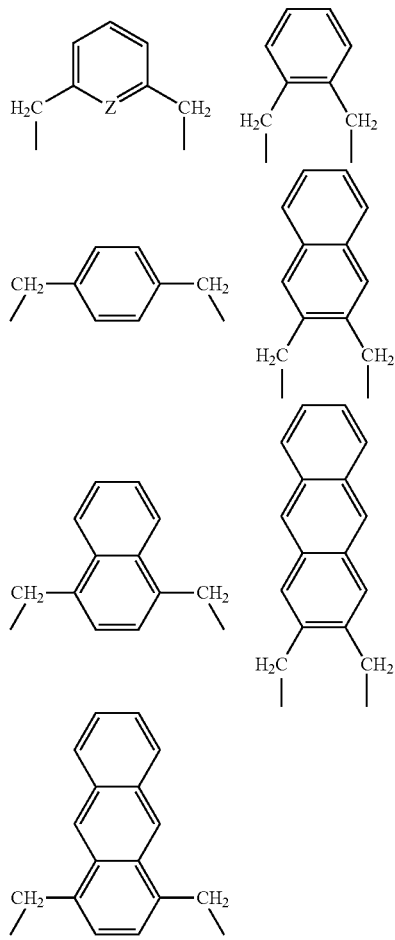

The disclosures of this description provide a method for producing an RNA interference agent, comprising a step of preparing a guide strand and a passenger strand that is a single-stranded oligonucleotide having one or two or more PAZ domain low-affinity units at the 3'-end, and forming double-stranded RNA by hybridization.

The disclosures of this description provide an oligonucleotide synthesis reagent represented by the following formula.

[Chem. 5]

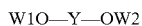

(where Y represents a $C_{1-4}$ alkylene group, W1 represents a hydrogen atom or hydroxyl protective group, and W2 is a hydrogen atom or phosphoramidite group or a linking group that binds to or has been bound to a solid-phase carrier).

The disclosures of this description provide a method for evaluating the function of a gene, wherein the evaluation method comprises a step of preparing the RNA interference agent disclosed in this description with the aforementioned gene as the target gene, and a step of introducing the RNA interference agent into a cell carrying the gene and evaluating changes in the cell.

The disclosures of this description provide a method for screening an RNA interference agent, wherein the screening method comprises a step of preparing one or two or more of the RNA interference agent disclosed in this description having respective candidate antisense sites for one or two or more different specific nucleotide sequences in a target gene, and a step of introducing the one or two or more RNA interference agents into a cell carrying the target gene and evaluating expression of the target gene in the cell.

The disclosures of this description provide a method for screening an RNA interference agent, wherein the screening method comprises a step of preparing one or two or more RNA interference agents each having a guide strand with an antisense site for a specific nucleotide sequence in a target gene and a passenger strand having one or two or more candidate PAZ domain low-affinity units at the 3'-end, and a step of introducing the one or two or more RNA interference agents into a cell carrying the target gene and evaluating a change in the cell.

BRIEF DESCRIPTION OF DRAWINGS

FIG. 2 shows an example of the RNA interference agent disclosed in this description;

FIG. 9 shows the results of microarray analysis using a specific filtering value of 1.

DESCRIPTION OF EMBODIMENTS

The disclosures of this description relate to an RNA interference agent for use in RNA interference, to a manufacturing method therefor and to the use of an RNA interference agent and the like. The off-target effect of a passenger strand can be controlled by using the single-stranded oligonucleotide disclosed in this description as the passenger strand of an RNA interference agent.

By controlling the off-target effect of an RNA interference agent, it is possible to achieve gene function analysis and drug screening with a high degree of reliability. It is also possible to perform highly safe gene therapy.

By controlling the off-target effect of an RNA interference agent, moreover, it is possible to increase the freedom of selection of antisense sites in guide strands, thereby increasing the RNA interference effect.

The disclosures of this description are explained in detail below with reference to FIG. 1 to FIG. 3 as necessary.

(Single-Stranded Oligonucleotide)

Figure 1:
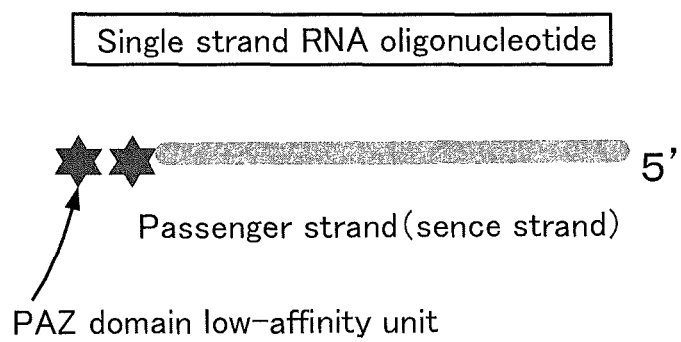
FIG. 1 shows one example of the single-stranded RNA disclosed in this description.

FIG. 1 shows one example of the single-stranded oligonucleotide disclosed in this description. As shown in FIG. 1, the single-stranded oligonucleotide disclosed in this description comprises one or two or more PAZ domain low-affinity units at the 3'-end. Although two PAZ domain low-affinity units are provided in FIG. 1, this is shown as a typical example and is not intended as a limitation.

As shown in FIG. 2, this single-stranded oligonucleotide disclosed in this description is used as the passenger strand of an RNA interference agent. The single-stranded oligonucleotide disclosed in this description is sometimes called a passenger oligonucleotide below.

The disclosures of this description focus on the PAZ domain structure in the RISC complex of the RNAi pathway. The PAZ domain recognizes 3'-end two-base overhang sites of siRNA. The PAZ domain has a hydrophobic pocket. A PAZ domain low-affinity unit may be a unit having a structure that interacts weakly with this pocket in comparison with units such as TT that make up the 3'-ends of conventional siRNA for example.

A PAZ domain low-affinity unit is a unit that causes an RNA strand to bind less easily to the PAZ domain of RISC than a strand provided with TT at the 3'-end when two of these units are provided at the 3' end of the RNA strand. A PAZ domain low-affinity unit can be obtained as follows for example. Double-stranded RNA comprising TT at the 3'-ends of the guide strand and passenger strand of double-stranded RNA having two units of each RNA single strand overhanging at the 3'-ends is prepared as control double-stranded RNA. Similarly, experimental double-stranded RNA is prepared that is identical to the control double-stranded RNA except in having two units of a PAZ domain low-affinity candidate introduced at the 3'-end of the guide strand. When the control double-stranded RNA and experimental double-stranded RNA are introduced under equivalent conditions into cells carrying a gene that is a target of expression suppression, the 3'-end candidate of an experimental double-stranded RNA that has a lower expression suppression effect on the target gene than the control double-stranded RNA is considered to be a PAZ domain low-affinity unit. More specifically, this is a unit with which no increase in the expression suppression effect occurs even if the introduced amount of the experimental double-stranded RNA is increased.

The cells may be human cells or non-human animal cells, and may also be other cells.

Such a PAZ domain low-affinity unit preferably contains a polar group. This is because it is commonly known that highly hydrophobic units have high affinity for the PAZ domain. The PAZ domain recognizes two-base overhangs at the 3'-end of the guide strand of siRNA. The PAZ domain of RISC has a hydrophobic pocket made up of a dense aggregation of hydrophobic residues having aromatic rings, and it is thought that it recognizes 2-base overhangs of the guide strand of siRNA by hydrophobic interaction. Therefore, it is sufficient that the 3'-end of the passenger strand be provided with a PAZ domain low-affinity unit with a structure that causes interactions with the hydrophobic pocket to be weaker than those of the 3'-end of the guide strand. This structure is not particularly limited, but may for example be a carboxyl group (—COOH), phosphate group (—PO$_3$H$_2$, —PO$_3$H—) or other acidic group that exhibits acidic properties in cells, or an amino group (—NH$_2$, —NH—) or other basic group that exhibits basic properties in cells. It may also be a hydroxy group (—OH) or ether bond (—O—) or the like.

Preferably, the PAZ domain low-affinity unit is represented by the following Formula (1) for example. When the PAZ domain low-affinity unit is at the terminus of the 3'-end, the right end of the following formula is a hydrogen atom or phosphate group.

[Chem. 6]

$$[\text{—X—Y—O—}]_n \qquad \text{Formula (1)}$$

In the Formula (1) above, X is a linking group, and Y is a group with 2 or more carbon atoms. In Formula (1) above, n represents the number of PAZ domain low-affinity units, and is an integer of 1 or 2 or more. When n is 2 or greater, the PAZ domain low-affinity units are provided consecutively. With such a PAZ domain low-affinity unit, synthesis is facilitated, and binding of the passenger oligonucleotide to the PAZ domain can be effectively suppressed.

Examples of PAZ domain low-affinity units having linking groups X include the bivalent groups described below for example. In the formulae below, R represents an alkyl group, acyl group or other substituent, and preferably represents a $C_{1-4}$ alkyl group or an acyl group having a $C_{1-4}$ alkyl group.

[Chem. 7]

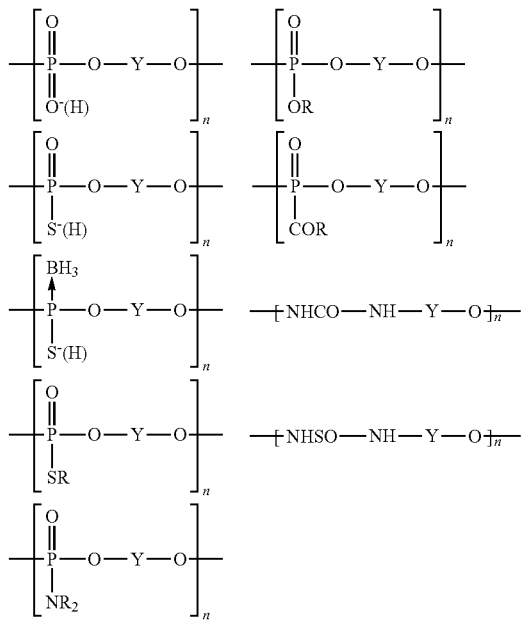

Each R represent any of alkyl any groups, acyl groups and so on.

Y may be any group having 2 or more carbon atoms, but preferably represents a $C_{1-4}$ alkylene group. It is preferably an alkylene group. It may be either linear or branched. The number of carbon atoms in the alkylene group is preferably 1 to 3, or more preferably 2 or 3, or still more preferably 2. A hydrogen atom of the alkylene group may be substituted, but is preferably unsubstituted.

A preferred PAZ domain low-affinity unit is represented by the following formula. In the following formula, Y and n are defined as in Formula (1), with Y being a $C_{1-3}$ unsubstituted linear or branched alkylene group. More preferably, it is an ethylene group with 2 carbon atoms.

[Chem. 8]

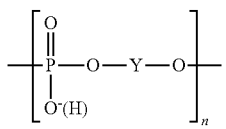

One or two or more of the PAZ domain low-affinity unit may be provided at the 3'-end of the passenger oligonucleotide. Preferably, two or more may be provided. When multiple PAZ domain low-affinity units are provided, they are preferably consecutive. The number of PAZ domain low-affinity units is preferably 4 or less, or more preferably 3 or less, or still more preferably 2. An oligonucleotide other than the PAZ domain low-affinity unit may also be provided at the 3'-end. Preferably, the PAZ domain low-affinity units are provided consecutively from the terminus of the 3'-end.

In addition to featuring this characteristic 3'-end, the passenger oligonucleotide may also be provided with other ordinary passenger oligonucleotide elements. That is, it is provided with a sense site that hybridizes specifically with an antisense site of the corresponding guide strand. The sense site is preferably a nucleotide sequence of RNA bases (A, G, C and U) that are completely complementary to the antisense site. Suitably modified bases as well as nucleotide derivatives and the like may be used in the sense site and the like for purposes such as increasing the stability of the RNA interference agent.

The length of the passenger oligonucleotide is not restricted, but when a PAZ domain low-affinity unit is included and one unit is considered as one nucleotide, the length is preferably 19 to 49 nucleotides, or more preferably 19 to 30 nucleotides, or still preferably 19 to 24 nucleotides, or yet more preferably 19 to 22 nucleotides. The ideal length is 21 nucleotides.

As shown in FIG. 1, because the passenger oligonucleotide has a PAZ domain low-affinity unit at its 3'-end, the 3'-end of the passenger oligonucleotide does not bind easily with the PAZ domain. As a result, as shown in FIG. 2 and FIG. 3, this passenger strand is selectively released from RISC when the passenger oligonucleotide is used as a passenger strand to form an RNA interference agent together with a guide strand. Consequently, no unintended single strand (passenger strand)-RISC complex is formed. That is, the target effect of the passenger oligonucleotide (off-target effect) is suppressed.

Moreover, synthesis costs are reduced because the passenger oligonucleotide is a simple unit containing a polar group. Moreover, the off-target effect can be suppressed by providing a simple polar unit at only the 3'-end of the passenger oligonucleotide.

The method of synthesizing this passenger oligonucleotide is explained in detail later.

(RNA Interference Agent)

The RNA interference agent disclosed in this description may be provided with a guide strand oligonucleotide having an antisense site for a specific nucleotide sequence of a target gene, together with a passenger oligonucleotide. FIG. 2 shows one example of an RNA interference agent. FIG. 2(a) and FIG. 2(b) show, respectively, an embodiment having no PAZ domain high-affinity unit at the 3'-end of the guide strand, and an embodiment having such a unit.

Figure 3:
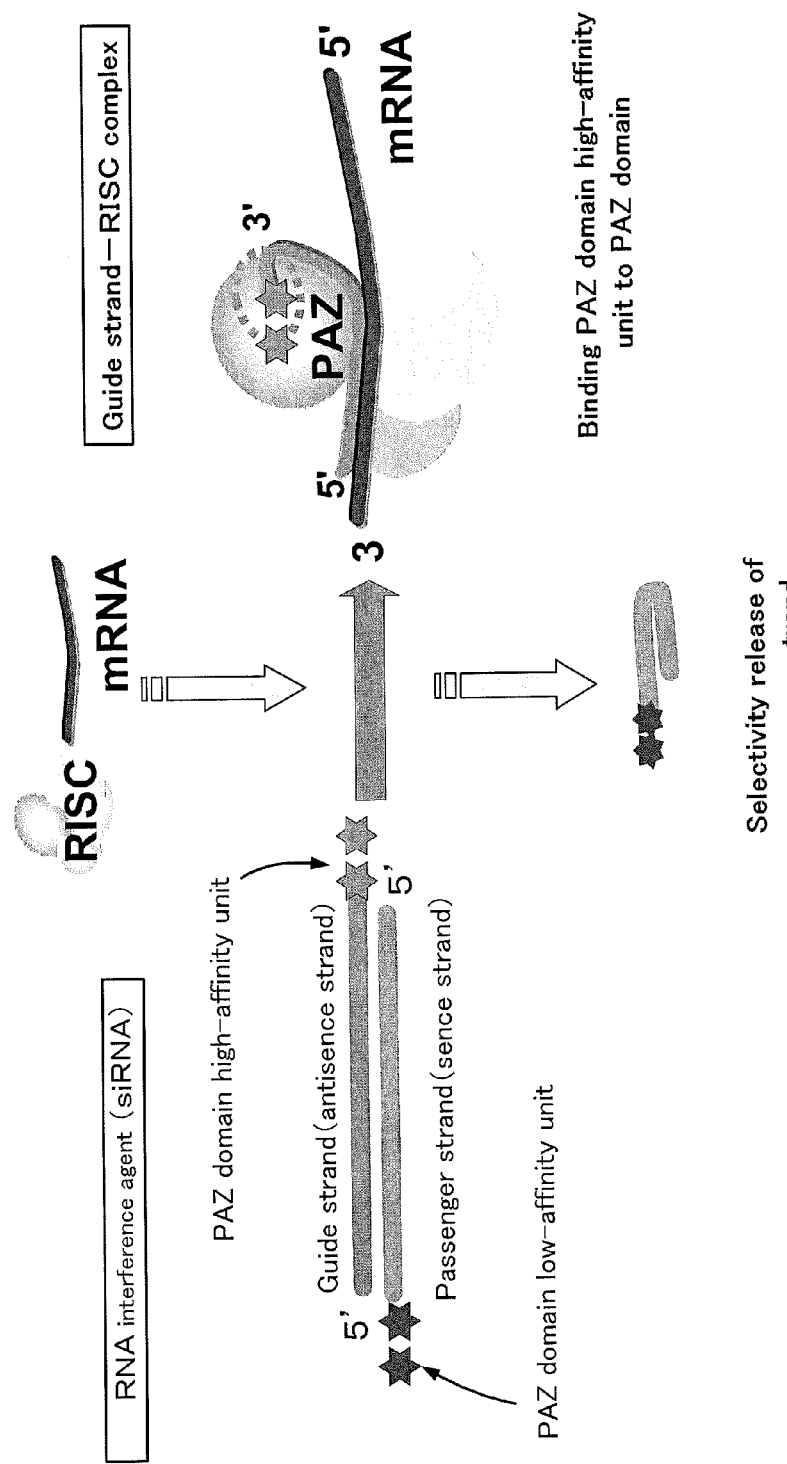
FIG. 3 shows an outline of the action of the RNA interference agent disclosed in this description.

With the RNA interference agent disclosed in this description, formation of an unintended RISC complex with the passenger strand is suppressed because the passenger oligonucleotide is provided as the passenger strand (see FIG. 3). The off-target effect is suppressed as a result. Consequently, expression of a target gene can be suppressed with high selectivity.

The guide strand of the RNA interference agent has an antisense site that hybridizes specifically with a specific nucleotide sequence (sense sequence) of a target gene. The antisense site here has a nucleotide sequence of RNA bases (A, G, C and U) that are preferably entirely complementary to a nucleotide sequence of the target gene. Modified bases, nucleotide derivatives and the like may be used appropriately in the antisense site and the like of the guide strand in order to increase the stability of the RNA interference agent.

The 3'-end of the guide strand has a dangling end that protrudes by one or two or more bases (preferably two bases) from the 5'-end of the passenger strand when the two are hybridized together. As in known conventional siRNA, the guide strand may be provided with UU, TT or other nucleotides at its 3'-end. The 3'-end of the guide strand may be provided with one or a combination of two or more of U, T or other bases.

The guide strand of the RNA interference agent may be provided with a PAZ domain high-affinity unit at the 3'-end. A PAZ domain high-affinity is a unit that causes an RNA strand to bind more easily to the PAZ domain of RISC than a strand provided with TT at the 3'-end when two such units are provided at the 3'-end of the RNA strand. A PAZ domain high-affinity unit can be obtained as follows for example. Double-stranded RNA comprising TT at the 3'-ends of the guide strand (which has an RNA nucleotide sequence complementary to the sense strand of a specific gene) and passenger strand of double-stranded RNA having two units of each RNA single strand overhanging at the 3'-ends is prepared as control double-stranded RNA. Similarly, experimental double-stranded RNA is prepared that is identical to the control double-stranded RNA except in having two units of a PAZ domain high-affinity candidate introduced at the 3'-end of the guide strand. When the control double-stranded RNA and experimental double-stranded RNA are introduced under equivalent conditions into cells carrying a gene that is a target of expression suppression, a unit at the 3'-end of an experimental double-stranded RNA that has a greater expression suppression effect on the target gene than the control double-stranded RNA is considered to be a PAZ domain high-affinity unit. More specifically, this is a unit with which an increase in the expression suppression effect occurs when the introduced amount of the experimental double-stranded RNA is increased.

A PAZ domain high-affinity unit can also be said to have a greater expression suppression effect than a PAZ domain low-affinity unit. A PAZ domain high-affinity unit can also be said to have lower polarity (to be more hydrophobic) than a PAZ domain low-affinity unit.

The backbone of a PAZ domain high-affinity unit may be either the sugar-phosphate backbone of a natural nucleotide or another, non-natural backbone. The unit itself may be a natural nucleotide, or a modified nucleotide, or a non-nucleotide compound.

A unit having a benzene-like backbone may be used favorably as such a PAZ domain high-affinity unit. A PAZ domain high-affinity unit is represented by Formula (2) below for example. When the PAZ domain high-affinity unit is at the end of the 3'-end, the right end of the following formula is a hydrogen atom or phosphate group. In Formula (2), m represents the number of PAZ domain high-affinity units, and is an integer of 1 or 2 or more. When m is 2 or more, the PAZ domain high-affinity units are provided consecutively.

[Chem. 9]

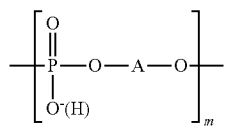

Formula(2)

(In the formula, A independently represents any of the formulae below, and m is integer of 1 or 2 or more).

[Chem. 10]

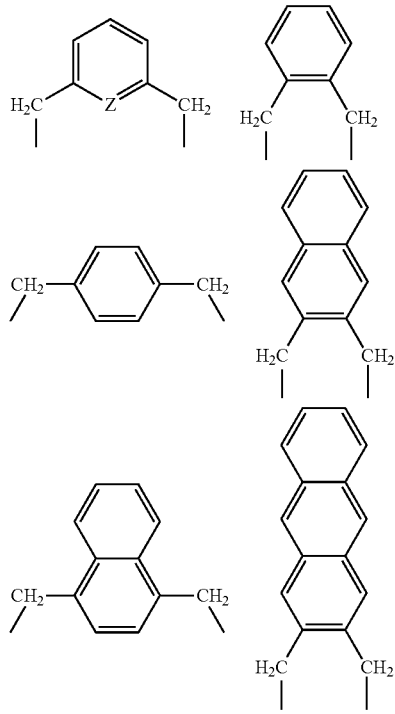

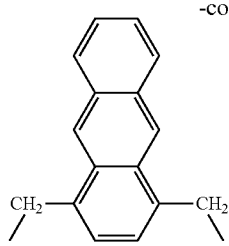

A unit having such a benzene-like backbone is described in detail for example in WO 2007/094135, and a person skilled in the art can supply such a unit as a PAZ domain high-affinity unit.

One or two or more of the PAZ domain high-affinity unit may be provided at the 3'-end of the passenger oligonucleotide. Preferably 2 or more can be provided. When there are multiple PAZ domain high-affinity units, they are preferably provided consecutively. The number of PAZ domain high-affinity units is preferably 4 or less, or more preferably 3 or less, or still more preferably 2.

(Method for Producing RNA Interference Agent)

The method for producing an RNA interference agent disclosed in this description may comprise a step of preparing a passenger oligonucleotide and a guide strand, and forming double-stranded RNA by hybridization. With this production method, it is possible to easily produce an RNA interference agent whereby the off-target effect is suppressed.

The passenger oligonucleotide may be synthesized by a known phosphoramidite method by using a phosphoramidite or CPG reagent to supply the PAZ domain low-affinity unit during synthesis of the 3'-end.

The compounds represented by the following formula for example may be used as phosphoramidite, CPG or other oligonucleotide synthesis reagents to supply the PAZ domain low-affinity unit.

[Chem. 11]

W1O—Y—OW2

In the formula above, $W_1$ may represent a hydrogen atom or hydroxy protecting group. The hydroxyl protecting group may be any group that protects a hydroxy group from unintended reactions. Various known conventional hydroxy protecting groups may be used as this hydroxy protecting group, with no particular limitations. Preferred protecting groups in the present invention are fluorenylmethoxycarbonyl (FMOC), dimethoxytrityl (DMT), tert-butyldimethylsilyl (TBDMS), monomethoxytrityl, trifluoroacetyl, levulinyl and silyl groups. A trityl group is preferred as the protecting group, which may be selected from dimethoxytrityl (DMT) and tert-butyldimethylsilyl (TBDMS) groups for example.

$W_2$ represents a hydroxy protecting group or phosphoramidite group or a linking group that binds to or is bound to a solid-phase carrier. A compound in which $W_2$ is a phosphoramidite group (amidite compound) can be used as a phosphoramidite reagent to synthesize an oligonucleotide by the phosphoramidite method. In the present invention, a phosphoramidite group may be represented by the following formula.

[Chem. 12]

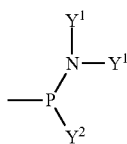

(In the formula, each $Y^1$ may be the same or different and independently represents a branched or linear $C_{1-5}$ alkyl group, and $Y^2$ represents a branched or linear $C_{1-5}$ alkyl group or an optionally substituted alkoxyl group).

In the formula above, $Y^1$ is not particularly limited but is preferably an isopropyl group, and examples of $Y^2$ include —OCH$_3$, —OCH$_2$CH$_2$CN, —OCH$_2$CHCH$_2$ and the like.

When $W_2$ is a linking group that binds to or is bound to a solid-phase carrier such as CPG, the compound is supported on the solid-phase carrier by binding between this linking group and an amino or other specific functional group on the solid-phase carrier. Moreover, in the case of a compound in which $W_2$ is a linking group bound to a solid-phase carrier in the formula above, because the —OYO— part of the PAZ domain low-affinity unit is bound to the solid-phase carrier via a specific linking group for the solid phase, this reagent can be used as a starting material for nucleic acid solid-phase synthesis of the passenger oligonucleotide. Multiple units of the PAZ domain low-affinity unit can be linked consecutively to this reagent by the phosphoramidite method or the like with a phosphoramidite reagent having a —OYO— part.

If a suitable number of PAZ domain low-affinity units are provided, moreover, an oligonucleotide of a specific length containing a sense unit can be synthesized using a commonly used ribonucleotide phosphoramidite reagent.

The solid-phase carrier here may be CPG (controlled pore glass), HCP (highly cross-linked polystyrene), or a kind of gel commonly used in polymer carriers. A suitable spacer may also be used in the solid-phase carrier. A linking group is a linker that links the compound to the solid-phase carrier. Known succinic acid ester linkers, oxalic acid ester linkers, silane diyl linkers, silyl linkers and the like may be used as such linking groups.

A reagent represented by such a formula is synthesized by a combination of known methods. For example, it may be synthesized according to the following scheme.

[Chem. 13]

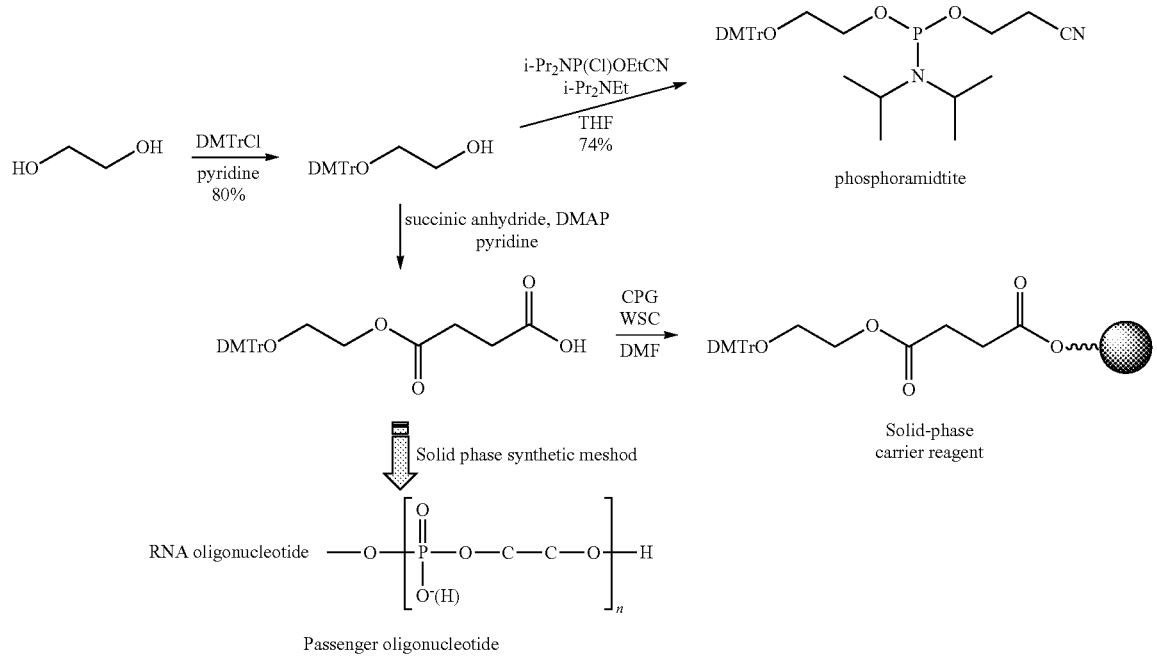

When introducing a PAZ domain high-affinity unit into the 3'-end of the guide strand, a unit with a benzene-like structure may be introduced by known methods as explained above. The antisense part of the guide strand is selected appropriately from the nucleotide sequence of the target gene.

(Method of Evaluating Gene Function)

The method of analyzing the function of a gene disclosed in this description may comprise a step of preparing the RNA interference agent disclosed in this description with the gene as a target gene, and a step of introducing the RNA interference agent into cells carrying the gene and evaluating changes in the cells. With this evaluation method, expression of the target gene alone can be suppressed with high selectivity because the off-target effect is controlled. This allows the gene to be evaluated accurately.

Common, well-known methods may be adopted for introducing the RNA interference agent into cells. Examples of cells include various cells including ex vivo human cells and non-human animal cells. The cells may also be in vivo non-human animal cells.

The evaluation items and evaluation methods in the step of evaluating changes in the cells may be determined appropriately by a person skilled in the art according to the type of target gene and the like. For example, in addition to evaluating the expression of a target gene in cells (whether or not expression has been suppressed, and to what degree), it is also possible to detect anticipated biological, chemical and/or physical changes in the cells. When in vivo cells are used as the cells, it is also possible to detect biological, chemical and/or physical changes in the non-human animal having the cells.

(Method of Screening RNA Interference Agent)

The method of screening an RNA interference agent disclosed in this description may comprise a step of preparing one or two or more of the RNA interference agents disclosed in this description having respective candidate antisense sites for one or two or more different specific nucleotide sequences in a target gene, and a step of introducing the one or two or more RNA interference agents into cells carrying the target gene and evaluating expression of the target gene in the cells. With this screening method, it is possible to accurately evaluate the expression suppression effect on a target gene of an RNA interference agent that has an antisense site candidate and a suppressed off-target effect. It is thus possible to efficiently screen effective antisense sites for RNA interference agents. It is also possible to screen RNA interference agents having effective antisense sites and suppressed off-target effects.

The various kinds of passenger oligonucleotides explained above may be used as passenger strands of RNA interference agents. The same applies to the guide strands. The antisense site is provided on the guide strand.

The cells into which the RNA interference agent is introduced may be various kinds of cells including ex vivo human cells and non-human animal cells. They may also be in vivo cells of non-human animals.

Methods of introducing RNA interference agents into cells and evaluating expression of target genes are well known to a person skilled in the art, and a person skilled in the art can select these appropriately according to the type of target gene and the form of the cells into which the RNA interference agent is introduced. Typically, a luciferase assay such as that shown in the examples or the like may be adopted.

(Method of Screening RNA Interference Agent)

The method of screening an RNA interference agent disclosed in this description may comprise a step of preparing one or two or more RNA interference agents having guide strands with antisense sites for specific nucleotide sequences in a target gene and passenger strands with one or two or more PAZ domain low-affinity unit candidates at the 3'-end, and a step of introducing the one or two or more RNA interference agents into cells carrying the target gene and evaluating changes in the cells. With this screening method, it is possible to screen PAZ domain low-affinity unit candidates that are effective for suppressing the off-target effect, and obtain an RNA interference agent whereby the off-target effect is suppressed. Typically, a luciferase assay such as that shown in the examples or the like is adopted.

A PAZ domain low-affinity unit candidate may be a unit containing an acidic group, a basic group or another group having polarity or highly polar group. The various embodiments of PAZ domain low-affinity units explained above may also be applied to the PAZ domain low-affinity unit candidate. In this way, it is possible to screen the most effective PAZ domain low-affinity units according to the type of gene and the type of cells.

In this screening method, the cells into which the RNA interference agent is introduced may be various cells including ex vivo human cells or non-human animal cells. They may also be in vivo cells of non-human animals. In this screening method, methods for introducing the RNA interference agent into the cells and evaluating expression of the target gene are well known to a person skilled in the art, and a person skilled in the art can select these appropriately according to the type of target gene and the cells into which the RNA interference agent is to be introduced.

EXAMPLES

The disclosures of this description are explained below with specific examples.

Example 1

Reagent Synthesis for PAZ Domain Low-Affinity Unit

Trityl (compounds 6 to 10), amidite (compounds 11 to 15) and CPG reagents (compounds 16 to 20) were synthesized according to the following schemes for the PAZ domain low-affinity unit.

[Chem 14]

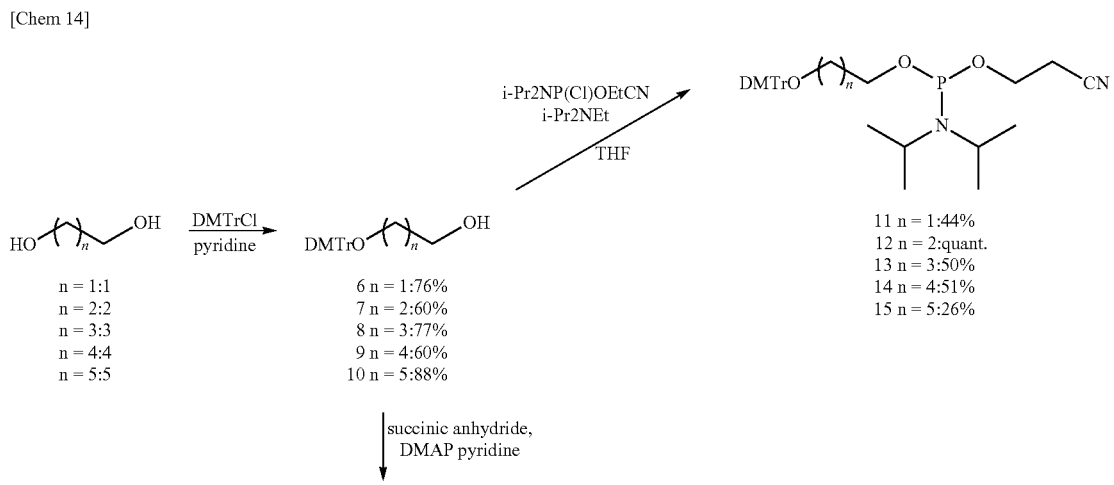

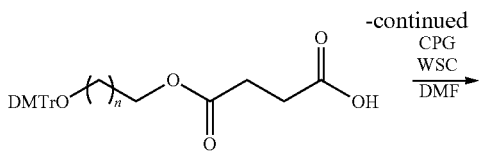 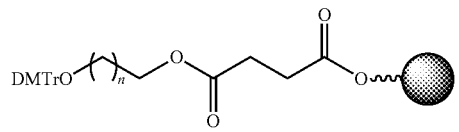

-continued 16 n = 1:17.6 mol/g
17 n = 2:
18 n = 3:
19 n = 4:
20 n = 5:

<Synthesis of Compounds 6 to 10>

Using Compounds 1 to 5 shown in the scheme as starting materials, one of the hydroxy groups was trityl protected with DMTrCl, and trityl compounds 6 to 10 were obtained. The detailed explanation of this is provided below. Here, a separate reaction was performed for each compound.

30 mL of dry pyridine was added to dissolve 1.00 g of thoroughly dried DMTrCl, and 3 equivalents each of ethylene glycol (Compound 1, 0.49 mL), propanediol (Compound 2, 0.64 mL), butanediol (Compound 3, 0.79 mL), pentanediol (Compound 4, 0.93 mL) and hexanediol (Compound 5, 1.05 g) were added and agitated for 3 hours at room temperature. This was then separated with ethyl acetate and distilled water, and the organic layer was washed with saturated $NaHCO_3$ aq and saturated NaCl aq, and dried by addition of anhydrous $Na_2SO_4$. The solvent was distilled off under reduced pressure, and the remainder was separated and purified by neutral silica gel chromatography (Hex: EtOAc=3:1) to obtain the target Compounds 6 (0.82 g, 76%), 7 (0.67 g, 62%), 8 (0.90 g, 77%), 9 (0.71 g, 60%) and 10 (1.09 g, 88%).

$^1$H NMR (400 MHz, $CDCl_3$) δ [ppm]:

(Compound 6): 7.45-7.20 (9H, m), 6.83 (4H, d, J=8.8 Hz), 3.79 (6H, s), 3.73 (2H, m), 3.26 (2H, t, J=4.8 Hz)

(Compound 7): 7.43-7.20 (9H, m), 6.83 (4H, d, J=8.4 Hz), 3.79 (6H, s), 3.76 (2H, t, J=5.8 Hz), 3.28 (2H, 5.8 Hz), 1.85 (2H, q, J=5.8 Hz)

(Compound 8): 7.44-7.20 (9H, m), 6.82 (4H, d, 7.6 Hz), 3.79 (6H, s), 3.64 (2H, s), 3.11 (2H, s), 1.68 (4H, s)

(Compound 9): 7.44-7.20 (9H, m), 6.82 (4H, d, 8.8 Hz), 3.79 (6H, s), 3.63 (2H, q, J-=6.1 Hz), 3.06 (2H, t, J=6.4 Hz), 1.66-1.17 (6H, m)

(Compound 10): 7.43-7.18 (9H, m), 6.82 (4H, d, J=8.4 Hz), 3.79 (6H, s), 3.62 (2H, q, J-=5.6 Hz), 3.05 (2H, t, J=6.0 Hz), 1.66-1.16 (8H, m)

<Synthesis of Compounds 11 to 15>

The remaining hydroxy groups of the trityl compounds 6 to 10 were phosphonated to produce amidite compounds 11 to 15. The details are given below. The reactions below were performed separately for each compound. Drying was performed in a glove bag under completely anhydrous conditions.

After drying in vacuum overnight, the Compounds 6 (0.294 g), 7 (0. g), 8 (0. g), 9 (0.172 g) and 10 (0. g) were dissolved in dry THF, and DIPEA (3 eq) and a phosphonation reagent (1.5 eq) were added to each. These were then removed from the glove bag, and agitated for 0.5 to 1 hour at room temperature. Elimination of the raw materials was confirmed by TLC (Hex:EtOAc=2:1). These were then extracted with $CHCl_3$ and saturated $NaHCO_3$ aq, and the organic layer was washed with saturated NaCl aq and dried by addition of anhydrous $Na_2SO_4$. The solvent was distilled off under reduced pressure, and the remainder was separated and purified by neutral silica gel chromatography (Hex: EtOAc=3:1) to obtain the target Compounds 11 (0.82 g, 76%), 12 (0.67 g, 62%), 13 (0.90 g, 77%), 14 (0.71 g, 60%) and 15 (1.09 g, 88%).

$^{31}$P NMR (160 MHz, $CDCl_3$) [ppm]: 149.21 (Compound 11), 149.13 (Compound 12), 147.92 (Compound 13), 147.90 (Compound 14), 147.76 (Compound 15)

<Preparation of CPG Carriers 16 to 20>

The trityl compounds 6 to 10 were succinylated and bound to CPG resin to obtain CPG reagents 16 to 20. The details are explained below.

After having been dried in vacuum overnight, the Compound 6 (0.29 g), Compound 7 (0.30 g), Compound 8 (0.24 g), Compound 9 (0.09 g) and Compound 10 (0.08 g) were dissolved in dry DMF (0.1 M solution), 0.5 eq of DMAP and 3 eq of anhydrous succinic acid were added, and the mixtures were agitated for 48 to 72 hours at room temperature in an Ar atmosphere. Elimination of the raw materials was confirmed by TLC (Hex:EtOAc=2:1). This was then extracted with EtOAc and saturated $NaHCO_3$ aq, and the organic layer was washed with saturated NaCl aq and dried with anhydrous $Na_2SO_4$. The solvent was distilled off under reduced pressure to produce respective succinyl compounds.

After drying in vacuum overnight, the succinyl compounds (assuming a yield of 100% in the succinylation reaction) were dissolved in dry DMF (0.02 M solution relative to CPG), and CPG resin (76 to 103 µmol/g, ¼ eq of raw material) was added and blended with the solution. WSC (4 eq of CPG) was added to this solution, and shaken for 72 to 120 hours at room temperature. This resin was washed with pyridine, 15 mL of a 0:1 M DMAP solution (pyridine:acetic anhydride=9:1) was added, and the mixture was shaken for 48 hours at room temperature. The resin was then washed with pyridine, EtOH and acetonitrile, and vacuum dried overnight in a dessicator. The activity of the resulting CPG reagents 16 to 20 was measured. The activity values were CPG resin 16: 56.6 µmol/g, 17: 52.2 µmol/g, 18: 23.2 µmol/g, 19: 29.4 µmol/g, 20: 53.1 µmol/g.

Activity was measured by the following method. 6 mg of the dried CPG resin was placed on a glass filter, a 3:2 solution of $HClO_4$:EtOH was poured in, and absorption of the UV 498 nm wavelength (wavelength of DMTr group) was measured in the filtrate and substituted in the following formula.

$$\frac{Abs(498\ nm) \times Vol.(solution)(mL) \times 14.3}{Weight(support)(mg)} = Activity(\mu mol/g) \quad [\text{Math. 1}]$$

Example 2

Oligonucleotide Synthesis and Preparation of RNA Interference Agent

Oligonucleotides having specific 3'-end dangling ends were synthesized in an automated nucleic acid synthesizer by the solid-phase phosphoramidite method. Guide strands (antisense strands) and passenger strands (sense strands) having the 3' dangling ends shown in the table below were synthesized. The nucleotide sequences of the guide strands and passenger strands apart from the 3' dangling ends are shown below. This RNA interference agent is designed to suppress expression of a gene coding for *Renilla* Luciferase, a fluorescent protein of *Renilla reniformis*.

A sense strand and antisense strand having the PB shown below at the 3'-end were also synthesized as described in WO 2007/094135.

[Chem. 15]

PB:

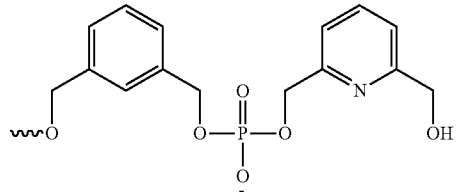

Figure 4:
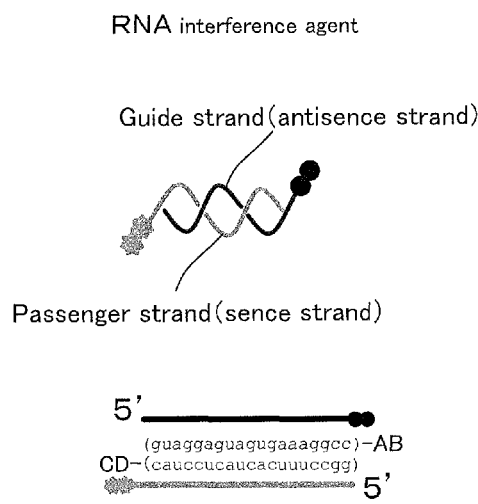
FIG. 4 shows an RNA interference agent prepared in an example.

The antisense strands and guide strands thus synthesized were combined in equal molar amounts, and annealed in various combinations of guide strands and passenger strands as shown in FIG. 4 to synthesize RNA interference agents of the examples and comparative examples.

Guide strand: 5'-gua gga gua gug aaa ggc c-3' (SEQ ID NO:1)
Passenger strand: 5'-ggc cuu uca cua cue cua c-3' (SEQ ID NO:2)

Solid-phase synthesis of nucleic acids was performed according to the phosphoramidite method, and after excision from the CPG resin, removal of the protecting groups and purification (PAGE or HPLC), the molecular weights of the target oligonucleotides were confirmed by MALDI-TOF/MS. The yields and percentage yields of the purified oligonucleotides are shown in Table 1 below.

TABLE 1

| 3' end | direction | yield(nmol) | M.W.(calcd) | M.W.(obsed) |
|---|---|---|---|---|
| TT | antisense | 56.2 | 6809 | 6810.7 |
| TT | sense | 102 | 6499.9 | 6502.1 |
| n = 2($E_2$) | antisense | 46 | 6448.9 | 6449.3 |
| n = 2($E_2$) | sense | 11.1 | 6139.8 | 6142.5 |
| n = 3($E_3$) | antisense | 36.4 | 6572.9 | 6577.6 |
| n = 3($E_3$) | sense | 16.3 | 6263.8 | 6264.6 |
| n = 4($E_4$) | antisense | 10.9 | 6699.9 | 6708.5 |
| n = 5($E_5$) | sense | 3.97 | 6511.7 | 6512.1 |

Example 3

Evaluation

The RNA interference agents prepared in Example 2 were evaluated as follows. Using the RNA interference agents of the examples and comparative examples, a Dual Luciferase reporter assay was performed using HeLa cells, and the knock-down effect was evaluated. The synthesized siRNA targeted *Renilla* Luciferase, and vectors expressing this gene and a control gene (firefly Luciferase) were transfected simultaneously together with the siRNA into HeLa cells to measure the knock-down effect. The specific operations and reagents are shown below. The results are given in FIG. 5 and FIG. 6.

(Operations)

The cells were seeded on a plate (4 to 5×10³ cells/well) and cultured for 24 hours, after which the respective amounts of siRNA and the vector were transfected with OPTI-MEM and transfast. The transfection time was one hour. After 24 hours of culture, the medium was suctioned out, after which the cells were stored overnight at −80° C., and evaluated the following day. Evaluation was performed according to the Promega protocols.

(Reagents, etc.)
Cells: HeLa cells
Plate: 96-well plate (BD falcon)
Medium: D-MEM (Wako)+10% BS (SIGMA) or OPTI-MEM (Invitrogen)
Transfection reagent: Tranfast™ (0.1 mM concentration, 0.3 µL/well)
siRNA: si RNA targeting *Renilla* gene (concentrations shown in figure)
Vectors: psiCHECK™-2 Vectors (Promega, 20 ng/well)
Assay kit: Dual-Glo™ Luciferase Assay System (Promega)

Figure 5:
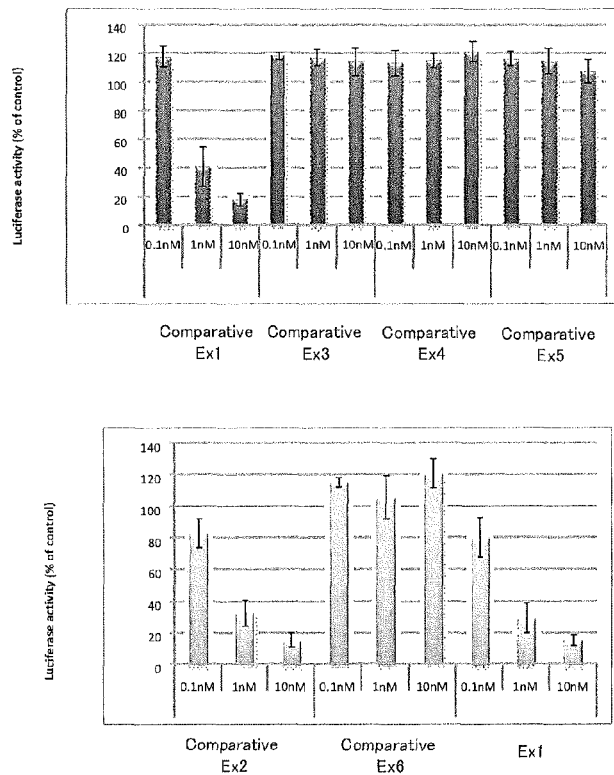
FIG. 5 shows evaluation results for RNA interference agents.
Figure 6:
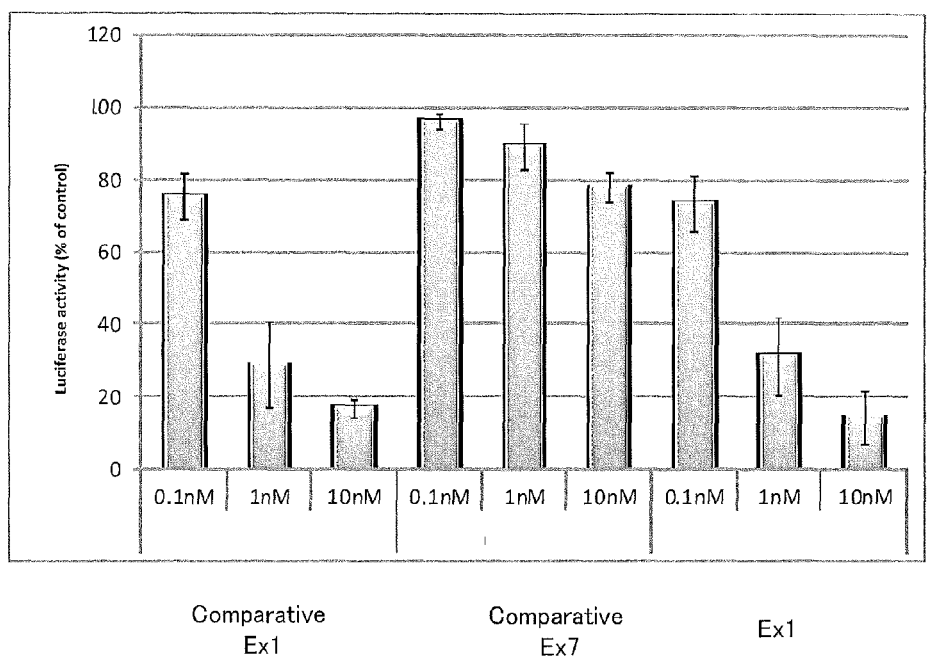
FIG. 6 shows evaluation results for RNA interference agents.

As shown in FIG. 5 and FIG. 6, when a highly polar unit is introduced into the 3'-end of an oligonucleotide, the function of the oligonucleotide as a guide strand is suppressed. This shows that the off-target effect of the passenger strand is suppressed by introducing such a unit into the 3'-end of the passenger strand.

Example 4

In this example, the suppression effect on the off-target effect of the passenger strand of introducing a highly polar PAZ domain low-affinity unit into the 3'-end of the passenger strand was confirmed by microarray analysis. For the operations, the RNA interference agent of these disclosures (siRNA, designed to suppress expression of a gene coding for *Renilla* Luciferase, a fluorescent protein of *Renilla reniformis* as in Examples 2 and 3) and control siRNA were introduced into cells, total RNA was extracted, cDNA was prepared, and gene expression was confirmed with a microarray.

(Transfection)

HeLa cells that had been successively cultured in cell culture liquid containing 10% BS (D-MEM, Wako) were used. On the day before transfection they were seeded to 5000 cells/well on a 24-well plate. The next day, transfection was performed using OPTI-MEM (Invitrogen) under three sets of conditions: A: plasmid only (negative control); B: plasmid+TT:TT siRNA (100 nM) (positive control); and C: plasmid+TT:EE siRNA (100 nM) (RNA interference agent of disclosures). The "EE" of TT:EE in the C plasmid represents two linked units of ethylene glycol.

The transfected plasmid was the Promega psi-CHECK-2 vector, and the siRNA sequences were antisense strand: 5'-guaggaguagugaaaggcc-3' (SEQ ID NO:1) and sense strand: 5'-ggccuuucacuacuccuac-3' (SEQ ID NO:2). After one hour, serum-containing medium was added (500 µl/well). After 24 hours, the cells were collected with trypsin-EDTA solution (Invitrogen).

(RNA Extraction)

Total RNA was extracted from the collected cells using a QIAGEN RNeasy mini kit with reference to the recommended protocols. When the absorbancy of the resulting total RNA solution was measured, the results were A: 792.4 ng/μl, B: 941.6 ng/μl and C: 642.8 ng/μl.

(Microarray Analysis)

The total RNA extracted from the cells was shipped to Hokkaido System Science Co., Ltd. under refrigeration with dry ice, and a microarray analysis (Agilent Technologies SurePrint G3 Human GE Ver. 2.0 8×60 K 1 color) was commissioned. This commissioned analysis included a quality inspection of the total RNA, synthesis of cDNA from the total RNA, tRNA labeling (Cy3) and amplification, hybridization, and scanning operations. The delivered raw data were analyzed in detail with GeneSpring 12.5 microarray data analysis software. First, all of the raw data were normalized (chip-to-chip correction) at the 75th percentile. The expressed amounts were then filtered (20th to 100th percentile).

(Comparison of Expressed Amounts of Housekeeping Genes)

Because on some chips the probe sequences of housekeeping genes were different on the Agilent Technologies DNA microarray even though the genes were identical, these were compared to guarantee the reliability of the array data. As a result, given condition A as 1, the comparative expressed amounts on all the chips ranged from 0.85 to 1.15. Thus, expressed amounts within this range were subsequently treated as the same. Put another way, genes the expressed amount of which ranged below 0.85 or above 1.15 were treated as being different.

(Comparison of Microarray Analysis Results and Results of Relative Gene Expression Assay by Real-Time RT-PCR)

Figure 7:
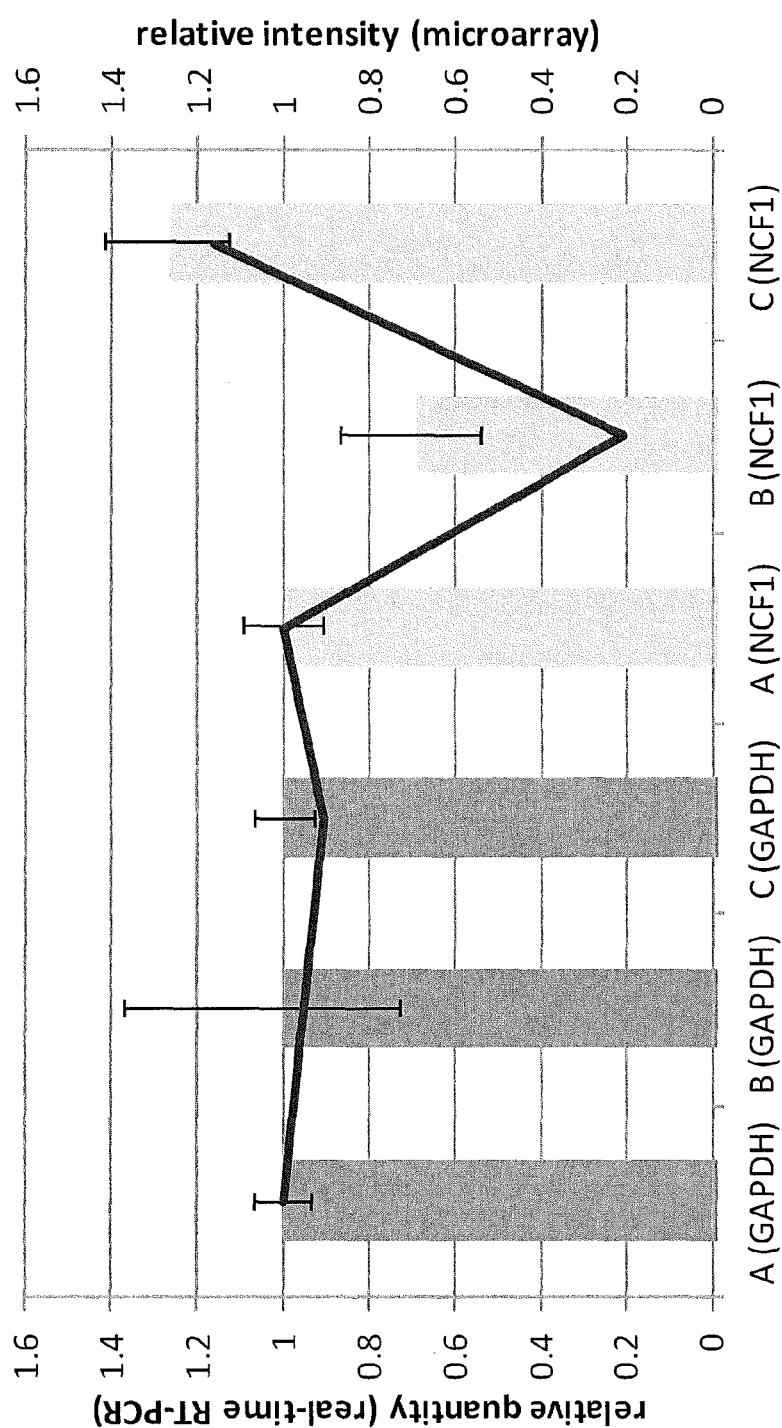
FIG. 7 shows the results of an evaluation of correlation between different arrays (A, B, C) in microarray analysis.

Transfection was performed under the conditions A, B and C described above, total RNA was extracted from the cells, and a relative assay was performed by real-time RT-PCR based on the Ct values for the GAPDH gene and NCF1 gene. A TaKaRa One Step SYBR PrimeScript PLUS RT-PCR Kit (SYBR Green I detection system) was used for real-time RT-PCR, and the PCR reaction was performed in accordance with the recommended protocols. As a result, correlation of the NCF1 gene was confirmed as shown in FIG. 7 when the GAPDH gene was controlled. The primer sequences used for the two genes in the PCR reaction were as follows.

```
                                        (SEQ ID NO: 3)
         GAPDH-For        TATAAATTGAGCCCGCAGCC (SEQ ID NO: 4)
         GAPDH-Rev        CCATGGTGTCTGAGCGATGT (SEQ ID NO: 5)
         NCF1-For         GAAGGTGTCCCCCATGACTG (SEQ ID NO: 6)
         NCF1-Rev         TCCAGTGCATTTAAGGCGCA
```

(Numerical Interpretation 1 by Microarray Data Analysis)

Figure 8:
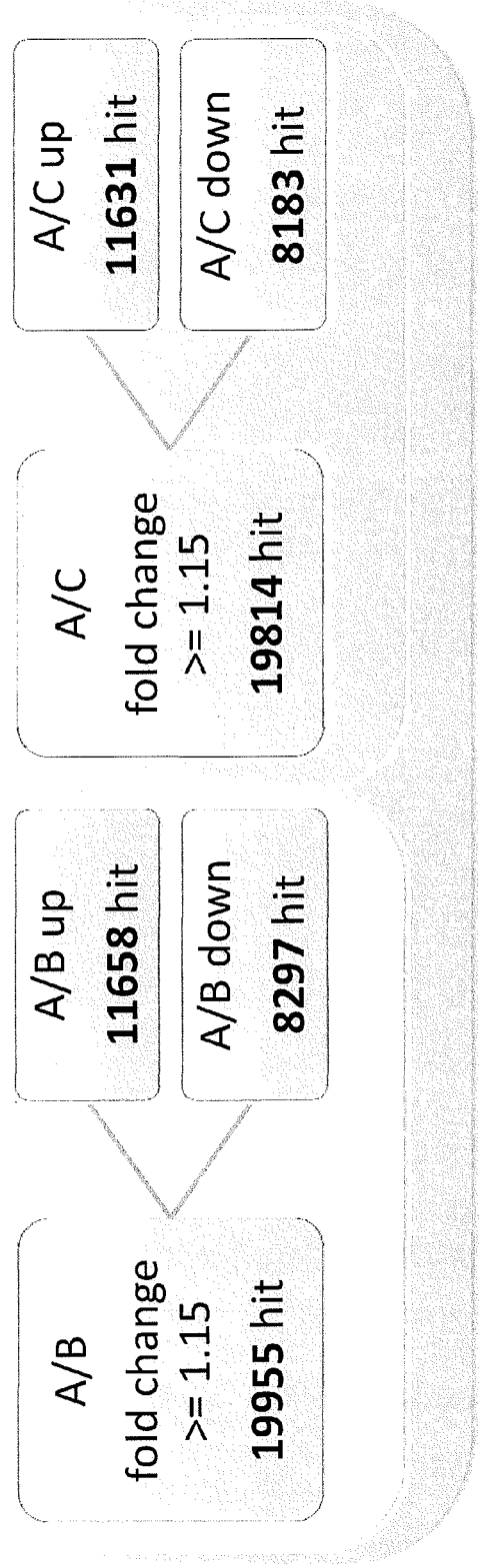
FIG. 8 shows the results of microarray analysis using a specific filtering value of 1.15.

The microarray data obtained through the filtering described above were subjected to fold change analysis. The designated value during fold change filtering was set at 1.15 based on the comparative result for expressed amounts of housekeeping genes. The results are shown in FIG. 8.

As a result, different amounts of expression were seen with A (negative control) and B (positive control) (hereunder, A/B) for 19955 genes, of which 11658 genes exhibited reduced expression with B rather than A (A/B up in figure), and 8297 exhibited increased expression (A/B down in figure). The number of genes exhibiting differences in expression between A and C (the RNA interference agent of these disclosures) was 19814, of which 11631 exhibited reduced expression with C in comparison to A (A/C up in figure), and 8183 exhibited increased expression (A/C down in figure). These numerical differences may not all be attributable to the off-target effect of the sense strand and the suppression of this effect (because there is also an off-target effect from the antisense strand), but taking A as the control, more expression suppression was seen with B than with C for 27 genes, confirming suppression of the off-target effect by the RNA interference agent of these disclosures.

(Numerical Interpretation 2 by Microarray Data Analysis)

When the designated value for fold change filtering was set at 1 as shown in FIG. 9, 26436 out of a total of 44428 genes exhibited reduced expression with B rather than A (AB up in figure), while 17992 exhibited increased expression (A/C down in figure), and 21476 gene exhibited reduced expression with C rather than A (A/C up in figure), while 22952 exhibited increased expression (A/C down in figure). Not all of the numbers are attributable to suppression of the off-target effect of the sense strand as discussed above, but taking A as the control, more expression suppression was seen with B than with C for 4960 genes, confirming suppression of the off-target effect by the RNA interference agent of these disclosures.

(Comparison of Expressed Amounts of Specific Genes by Microarray Data Analysis)

Specific genes that were highly likely targets were identified by a BLAST search using the sense strand sequence of the RNA interference agent (C) of these disclosures. The expressed amounts of each gene were compared from the microarray data. A site where the single-stranded siRNA recognizes and cleaves the target mRNA has already been found between No. 10 and No. 11 from the 5' end. The expression strengths of four kinds of genes with matching complementary sequences including this site and the seed region (Nos. 2 to 8) were compared under conditions A to C (with A as the benchmark). The results are shown in FIG. 10.

Figure 10:
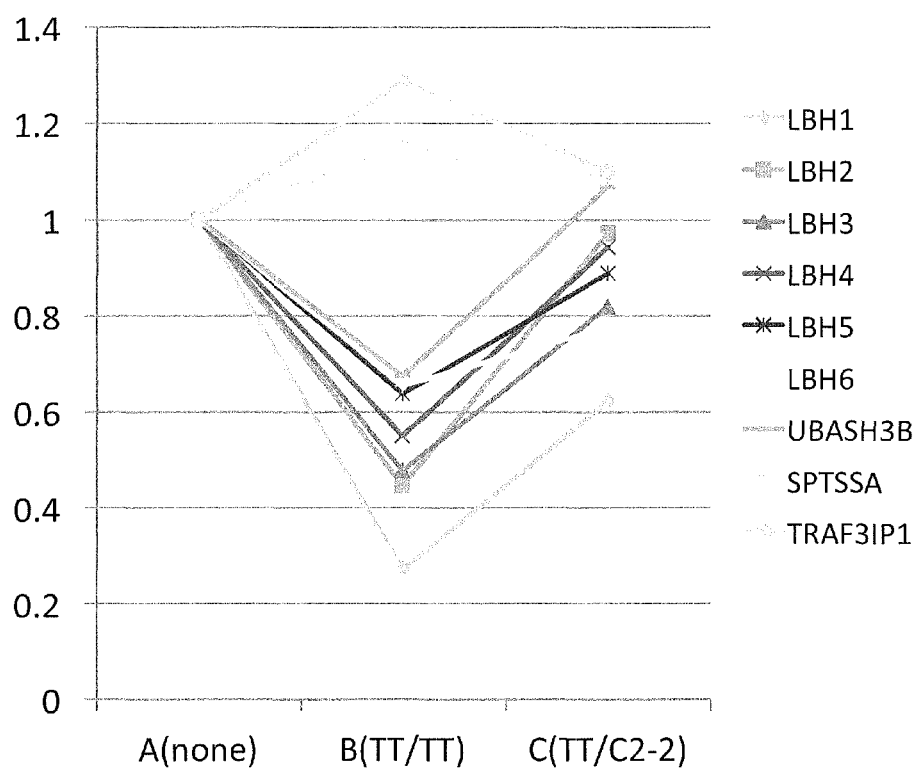
FIG. 10 shows the results of an evaluation of suppression of the off-target effect by the sense strand of an RNA interference agent on 9 spots of an array.

As shown in FIG. 10, the 9 spots on the microarray corresponding to these four types of genes exhibited low fluorescence intensity in array analysis B, but in array analysis C the fluorescence intensity increased, approaching the results of array analysis A (negative control). These results confirm that the off-target effect was avoided in the microarray C. The probe sequences for detecting each gene on the microarray are shown below (60-mer) (SEQ ID NO:7 to 12).

TABLE 2

| PROBE | 5'⇒3' | SEQ ID |
|---|---|---|
| LBH1 | ATAACTGCGAAGAGACAGCGAAAGAAAATAAAGA GCAGTAGAGTCCCTGTGGACTCCCAT | 7 |
| LBH2, 3, 5, 6 | CTTGTAAACTGCGTAACAAATCTACTTTGTGTAT GTGTCTGTTTATGGGGTGGTTTATT | 8 |
| LBH4 | AGAGTGAGCCGCAATTGTTCTGAAAATGTCAAAC GAGGCTTCTGTTTTGCACCTGCAGAT | 9 |
| UBASH3B | CATTGTAATTACAGATGCACCTTTCAGGAGCATC TCCATTAAATGGTGGCATAGATGATTT | 10 |
| SPTSSA | TTAGTTTAATGATTGTAATGGGTGCTGCATTTGC ACATTGCATTAAGTTATGATGAGACG | 11 |
| TRAF3IP1 | CAAATGACTTAGCCATGACCCTGAATGGACCTTG TTTTACTTCAAGTTGAGATGTCTGCC | 12 |

Sequence Listing Free Text
SEQ ID NOS:1, 2: siRNA
SEQ ID NOS:3 to 6: primers
SEQ ID NOS:7 to 12: probes

The invention claimed is:

1. A method comprising:
   modifying the 3'-end of a single-stranded passenger oligonucleotide with at least one unit represented by the following Formula (1) sufficient to suppress an off-target effect:

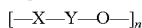   Formula (1)

where X is a linking group, Y represents an alkylene group with 2 carbon atoms, and n is an integer of 2 or more.

2. The method according to claim 1, wherein the at least one unit is represented by the following formula:

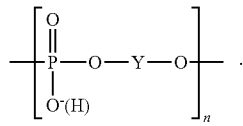

3. The method according to claim 1, wherein n represents 2.

4. A method for performing RNA interference, comprising:
   introducing an RNA interference agent into a cell carrying a gene that is a target of expression suppression, the RNA interference agent comprising:
   a guide strand oligonucleotide having an antisense site for a specific nucleotide sequence of the target gene and at least one PAZ domain high-affinity unit at the 3'-end; and
   a passenger strand oligonucleotide having at least one PAZ domain low-affinity unit at the 3'-end and that hybridizes specifically with the antisense site,
   wherein:
   the PAZ domain high-affinity unit has an affinity equal to or higher than the affinity of TT strand to PAZ domain, and
   the PAZ domain low-affinity unit is represented by the following Formula (1):

   Formula (1)

where X is a linking group, Y represents an alkylene group with 2 carbon atoms, and n is an integer of 2 or more.

5. The method according to claim 4, wherein the PAZ domain low-affinity unit is represented by the following formula:

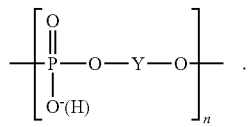

6. The method according to claim 4, wherein n represents 2.

7. The method according to claim 4, wherein the PAZ domain high-affinity unit is represented by the following Formula (2):

Formula(2)
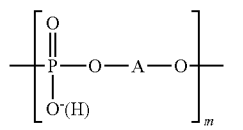

where A independently represents any of the following formulae, and m is an integer of 1, 2 or more:

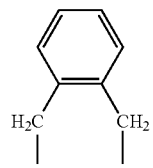

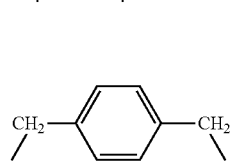

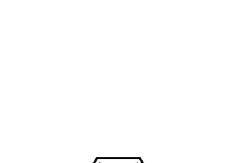

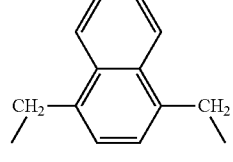

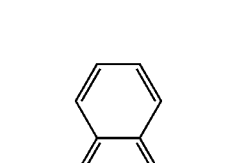

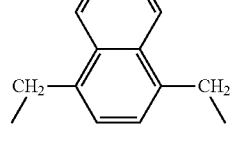

8. A method for producing an RNA interference agent, the method comprising:
   forming a double-stranded RNA by hybridizing specifically:
   a guide strand oligonucleotide having an antisense site for a specific nucleotide sequence of a target gene and at least one PAZ domain high-affinity unit at the 3'-end, and
   a passenger strand oligonucleotide having at least one PAZ domain low-affinity unit at the 3'-end and that hybridizes specifically with the antisense site
   wherein:
   the PAZ domain high-affinity unit has an affinity equal to or higher than the affinity of TT strand to PAZ domain, and
   the PAZ domain low-affinity unit is represented by the following Formula (1):

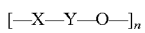   Formula (1)

where X is a linking group, Y represents an alkylene group with 2 carbon atoms, and n is an integer of 2 or more.

9. A method of screening an RNA interference agent, the method comprising:
   producing one or two or more RNA interference agents according to claim 8, having respective candidate antisense sites for one or two or more different specific nucleotide sequences in a target gene; and introducing the one or two or more RNA interference agents into a cell carrying the target gene and evaluating expression of the target gene in the cell.

10. The method according to claim 1, wherein X is an acidic group.

11. The method according to claim 1, wherein X is a basic group.

12. The method according to claim 4, wherein X is an acidic group.

13. The method according to claim 4, wherein X is a basic group.

* * * * *

SEQUENCE LISTING

<160> NUMBER OF SEQ ID NOS: 12

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
guaggaguag ugaaaggcc					19

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
ggccuuucac uacuccuac					19

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tataaattga gcccgcagcc					20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ccatggtgtc tgagcgatgt					20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gaaggtgtcc cccatgactg					20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tccagtgcat ttaaggcgca					20

<210> SEQ ID NO 7
<211> LENGTH: 60
<212> TYPE: DNA
<213> ORGANISM: Artificial Sequence
<220> FEATURE:
<223> OTHER INFORMATION: probe

<400> SEQUENCE: 7
ataactgcga agagacagcg aaagaaaata aagagcagta gagtccctgt ggactcccat    60

<210> SEQ ID NO 8
<211> LENGTH: 60
<212> TYPE: DNA
<213> ORGANISM: Artificial Sequence
<220> FEATURE:
<223> OTHER INFORMATION: probe

<400> SEQUENCE: 8
cttgtaaact gcgtaacaaa tctactttgt gtatgtgtct gtttatgggg gtggtttatt    60

<210> SEQ ID NO 9
<211> LENGTH: 60
<212> TYPE: DNA
<213> ORGANISM: Artificial Sequence
<220> FEATURE:
<223> OTHER INFORMATION: probe

<400> SEQUENCE: 9
agagtgagcc gcaattgttc tgaaaatgtc aaacgaggct tctgttttgc acctgcagat    60

<210> SEQ ID NO 10
<211> LENGTH: 60
<212> TYPE: DNA
<213> ORGANISM: Artificial Sequence
<220> FEATURE:
<223> OTHER INFORMATION: probe

<400> SEQUENCE: 10
cattgtaatt acagatgcac ctttcaggag catctccatt aaatggttca tagatgattt    60

<210> SEQ ID NO 11
<211> LENGTH: 60
<212> TYPE: DNA
<213> ORGANISM: Artificial Sequence
<220> FEATURE:
<223> OTHER INFORMATION: probe

<400> SEQUENCE: 11
ttagtttaat gattgtaatg ggtgctgcat ttgcacattg cattaagtta tgatgagacg    60

<210> SEQ ID NO 12
<211> LENGTH: 60
<212> TYPE: DNA
<213> ORGANISM: Artificial Sequence
<220> FEATURE:
<223> OTHER INFORMATION: probe

<400> SEQUENCE: 12
caaatgactt agccatgacc ctgaatggac cttgttttac ttcaagttga gatgtctgcc    60